US010456113B2

(12) United States Patent
Moshavegh et al.

(10) Patent No.: US 10,456,113 B2
(45) Date of Patent: Oct. 29, 2019

(54) WALL-TO-WALL VESSEL SEGMENTATION IN US IMAGING USING A COMBINATION OF VFI DATA AND US IMAGING DATA

(71) Applicant: B-K MEDICAL APS, Herlev (DK)

(72) Inventors: Ramin Moshavegh, Kobenhavn (DK); Jorgen Arendt Jensen, Horsholm (DK); Bo Martins, Herlev (DK)

(73) Assignee: B-K Medical Aps, Herlev (DK)

( * ) Notice: Subject to any disclaimer, the term of this patent is extended or adjusted under 35 U.S.C. 154(b) by 437 days.

(21) Appl. No.: 15/259,231

(22) Filed: Sep. 8, 2016

(65) Prior Publication Data
US 2018/0064421 A1    Mar. 8, 2018

(51) Int. Cl.
    *A61B 8/08*         (2006.01)
    *A61B 8/06*         (2006.01)
    *A61B 8/00*         (2006.01)

(52) U.S. Cl.
    CPC ............... *A61B 8/5223* (2013.01); *A61B 8/06* (2013.01); *A61B 8/0891* (2013.01); *A61B 8/5246* (2013.01); *A61B 8/463* (2013.01); *A61B 8/5269* (2013.01)

(58) Field of Classification Search
CPC ... A61B 8/5223; A61B 8/0891; A61B 8/5246; A61B 8/06; A61B 8/5269; A61B 8/463; G06T 7/0016; G06T 7/0012
USPC ........................................................ 600/441
See application file for complete search history.

(56) References Cited

U.S. PATENT DOCUMENTS

| 6,859,659 | B1 | 2/2005 | Jensen | |
|---|---|---|---|---|
| 2008/0193014 | A1* | 8/2008 | Ecker | G06K 9/0014 382/173 |
| 2010/0222671 | A1* | 9/2010 | Cohen | A61B 5/0044 600/424 |

(Continued)

OTHER PUBLICATIONS

Fenster et al., "Three-dimensional ultrasound imaging", 2001, Phys. Med. Biol., vol. 46., pp. R67-R99 (Year: 2001).*

(Continued)

*Primary Examiner* — Tse W Chen
*Assistant Examiner* — Jason M Ip
(74) *Attorney, Agent, or Firm* — Anthony M. Del Zoppo, III; Daugherty & Del Zoppo Co. LPA (57) ABSTRACT

An ultrasound imaging system includes an image processor and a velocity processor configured to process beamformed ultrasound data representing structure flowing through a tubular object and generate, respectively, an image indicative of the tubular object and vector flow imaging data indicative of the structure flowing through the tubular object. The system further includes a segmentation processor configured to segment the tubular object from the image based on a combination of both the vector flow imaging data and the image, wherein a resulting segmentation extends from wall-to-wall of the tubular object. The system further includes a display configured to display the image with the segmentation and the vector flow imaging data superimposed thereover, with the vector flow imaging data extending from wall-to-wall within the tubular object. The system further includes the automatic computation of largest vessel diameter (Dmax), and/or quantitative flow measures such as Peak systolic velocity (PSV) and/or volume flow.

21 Claims, 7 Drawing Sheets

(56) References Cited

U.S. PATENT DOCUMENTS

| | | | | |
|---|---|---|---|---|
| 2011/0208056 | A1* | 8/2011 | Datta | A61B 8/06 600/441 |
| 2011/0311066 | A1* | 12/2011 | Nagy | H04B 3/23 381/66 |
| 2012/0215110 | A1* | 8/2012 | Wilkening | A61B 8/488 600/453 |
| 2014/0073923 | A1* | 3/2014 | Haugaard | A61B 8/06 600/441 |
| 2014/0221838 | A1* | 8/2014 | Loupas | G01S 15/8984 600/454 |
| 2014/0276072 | A1* | 9/2014 | Martins | A61B 8/488 600/454 |
| 2016/0151038 | A1* | 6/2016 | Govinahallisathyanarayana | G01S 15/8979 600/454 |

OTHER PUBLICATIONS

Evans et al., "Ultrasonic colour Doppler imaging," 2011, Interface Focus, vol. 1 pp. 490-502 (Year: 2011).*

Noble et al., "Ultrasound image segmentation: a survey," Aug. 2006, IEEE Transactions on Medical Imaging, vol. 25, No. 8, pp. 987-1010 (Year: 2006).*

Loizou, "A review of ultrasound common carotid artery image and video segmentation techniques," 2014, Med. Biol. Eng. Comput., vol. 52, pp. 1073-1093 (Year: 2014).*

Molinari et al., "A state of the art review on intima-media thickness (IMT) measurement and wall segmentation techniques for carotid ultrasound," 2010, Computer Methods and Programs in Biomedicine, vol. 100, pp. 201-221 (Year: 2010).*

Powers et al., "Medical ultrasound systems," 2011,Published Online May 18, 2011, Interface Focus, vol. 1, pp. 477-489, 2011 (Year: 2011).*

York et al., "Ultrasound Processing and Computing: Review and Future Directions," 1999, Annu. Rev. Biomed. Eng., vol. 01, pp. 559-588 (Year: 1999).*

Moshavegh et al. "Automated segmentation of free-lying cell nuclei in Pap smears for malignancy-associated change analysis," Aug. 28-Sep. 1, 2012, in Proc. 34th Annual International Conference of the IEEE EMBS, San Diego, California pp. 5372-5375 (Year: 2012).*

Sultana et al. "Registration of retinal images using blood vessel features," Sep. 14-15, 2015, in Proc. 2015 International Symposium on Advanced Computing and Communication, India, pp. 224-229 (Year: 2015).*

Li et al. "Vessel Tracking Algorithms in Ultrasound Imaging," May 16-18, 2008, in Proc. 2nd International Conference on Bioinformatics and Biomedical Engineering, China, pp. 2481-2484 (Year: 2008).*

Huang et al. "Analysis of Tumor Vascularity Using Three-Dimensional Power Doppler Ultrasound Images", Mar. 2008, IEEE Transactions on Medical Imaging, vol. 27, No. 3, pp. 320-330 (Year: 2008).*

Eiho et al. "Detection of coronary artery tree using morphological operator," 1997, Computers in Cardiology, vol. 24, pp. 525-528 (Year: 1997).*

Santos et al. "A novel automatic algorithm for the segmentation of the lumen of the carotid artery in ultrasound B-mode images," 2013, Expert Systems with Applications, vol. 40, pp. 6570-6579 (Year: 2013).*

Ramasamy et al. "Automated Lumen Segmentation and Estimation of Numerical Attributes of Common Carotid Artery Using Longitudinal B-Mode Ultrasound Images," Jan. 16-18, 2013, in Proc. 2013 IEEE Point-of-Care Healthcare Technologies, Bangalore, India, pp. 306-309 (Year: 2013).*

Carvalho et al. "Lumen Segmentation and Motion Estimation in B-Mode and Contrast-Enhanced Ultrasound Images of the Carotid Artery in Patients With Atherosclerotic Plaque," Apr. 2015, IEEE Transactions on Medical Imaging, vol. 34, No. 4, pp. 983-993 (Year: 2015).*

Golemati et al. "Carotid artery wall motion estimated from B-mode ultrasound using region tracking and block matching," 2003, Ultrasound in Med. & Biol., vol. 29, No. 3, pp. 387-399 (Year: 2003).*

Gomez et al. "Computerized lesion segmentation of breast ultrasound based on marker-controlled watershed transformation," Jan. 2010, Med. Phys. vol. 37 No. pp. 82-95 (Year: 2010).*

Jensen et al. "Accuracy and sources of error for an angle independent volume flow estimator" Sep. 3-6, 2014, in Proc. IEEE International Ultrasonics Symposium Proceedings, Chicago, IL p. 1714-1717 (Year: 2014).*

Somasundaram et al. "A method for filling holes in objects of medical images using region labeling and run length encoding schemes," 2010, In Proc. National Conference on Image Processing (NCIMP), pp. 110-115 (Year: 2010).*

* cited by examiner

WALL-TO-WALL VESSEL SEGMENTATION IN US IMAGING USING A COMBINATION OF VFI DATA AND US IMAGING DATA

TECHNICAL FIELD

The following generally relates to ultrasound (US) imaging and more particularly to segmenting a vessel, wall-to-wall, in an ultrasound B-mode image/volume using a combination of 2-D/3-D velocity flow imaging (VFI) data and the ultrasound B-mode image/volume.

BACKGROUND

Figure 1:
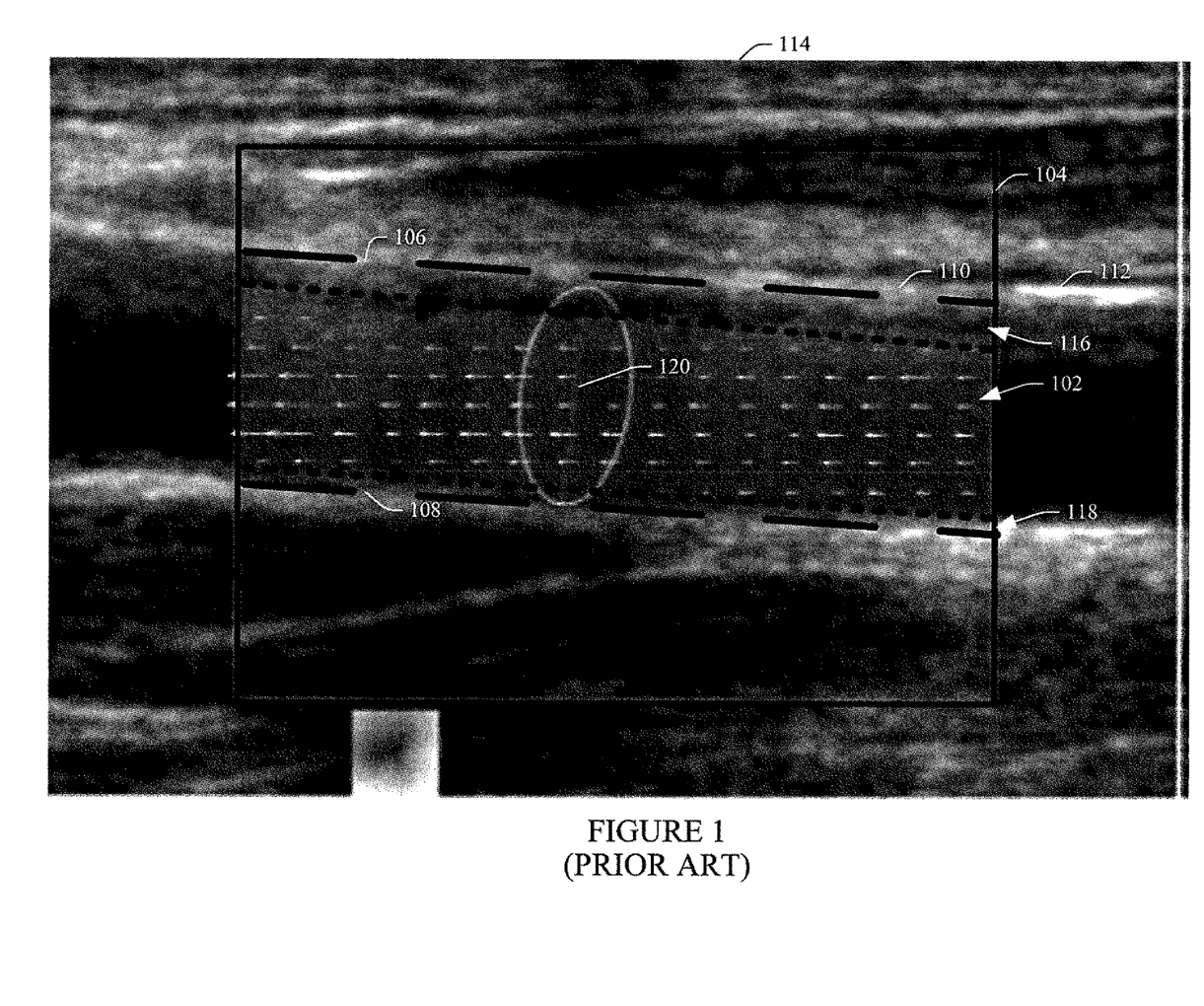
FIG. 1 illustrates an example prior art B-mode image with VFI data superimposed thereover.

Velocity flow imaging enables angle independent visualization of blood flow, allowing clinicians to visualize and estimate direction and velocity of blood flow in all directions and at any angle. However, today's commercial ultrasound scanners are not able to produce a wall-to-wall delineation of a vessel and present it simultaneously with VFI data superimposed within the entire vessel. FIG. 1 shows a prior art example in which VFI data 102 (the region approximately between dotted straight lines) for a region of interest 104 does not extend to the true walls 106 and 108 (approximated through the dashed straight lines) of a sub-portion 110 of a vessel 112 represented in a B-mode image 114. In this example, regions 116 and 118 between the dashed and dotted lines represent regions in the vessel sub-portion 110 without VFI data.

Furthermore, to obtain the full view of the velocities in the cardiac cycle, clinicians have to manually change parameters such as the pulse repetition frequency (PRF) when examining different magnitudes of velocities. For example, during systole, when higher velocities are present, a higher PRF is needed in order to estimate the right velocities. If the PRF is set too low, aliasing will occur as the blood scatterers are moving too fast to be detected. Unfortunately, it can be a troublesome maneuver to change back and forth between different PRF's at least since the full velocity range cannot be displayed simultaneously. As a consequence, clinicians typically select a static range. However, blood flow outside of the range can contain artifact and/or not even be detected. Unfortunately, this can lead to a misdiagnosis.

Furthermore, the clinician has to manually approximate, e.g., through visual inspection of the B-mode image 114, the location of the vessel walls to place a flow measurement line 120 along a cross-section of the vessel sub-portion 110 from one wall to the other wall for velocity flow measurements. However, this process can be tedious at least since the vessel walls 106 and 108 of the vessel sub-portion 110 are not clearly defined in the B-mode image 114. As a result, the velocity flow measurements may be taken using a part of the vessel sub-portion 110, where no VFI data is present (e.g., regions 116 and/or 118), and/or part of the anatomy outside of the vessel sub-portion 110 (e.g., non-vessel anatomy). Unfortunately, this may lead to erroneous and/or inaccurate flow measurements.

SUMMARY

Aspects of the application address the above matters, and others.

In one aspect, an ultrasound imaging system includes an image processor configured to process beamformed ultrasound data representing structure flowing through a tubular object and generate an image indicative of the tubular object based thereon. The ultrasound imaging system further includes a velocity processor configured to process the beamformed ultrasound data and generate vector flow imaging data indicative of the structure flowing through the tubular object based thereon. The vector flow imaging data includes at least an axial velocity component signal and one or more transverse velocity components indicating a direction and a speed of the structure flowing through the tubular object. The ultrasound imaging system further includes a segmentation processor configured to segment the tubular object from the image based on a combination of both the vector flow imaging data and the image, wherein a resulting segmentation extends from wall-to-wall of the tubular object. The ultrasound imaging system further includes a display configured to display the image with the segmentation and the vector flow imaging data superimposed thereover, with the vector flow imaging data extending from wall-to-wall within the tubular object.

In another aspect, a method includes generating an image indicative of a tubular object from beamformed ultrasound data representing structure flowing through the tubular object. The method further includes generating vector flow imaging data indicative of the structure flowing through the tubular object from beamformed ultrasound. The vector flow imaging data includes at least an axial velocity component signal and one or more transverse velocity components indicating a direction and a speed of the structure flowing through the tubular object. The method further includes generating a wall-to-wall segmentation of the tubular object from the image with a combination of the vector flow imaging data and the image. The method further includes visually presenting the image with the segmentation and the vector flow imaging data superimposed thereover, with the vector flow imaging data extending from wall-to-wall within the tubular object.

In another aspect, a computer readable storage medium is encoded with computer readable instructions. The computer readable instructions, when executed by a processor, causes the processor to: construct an image indicative of a tubular object from beamformed ultrasound data representing structure flowing through the tubular object, estimate vector flow imaging data indicative of the structure flowing through the tubular object from beamformed ultrasound, wherein the vector flow imaging data includes at least an axial velocity component signal and one or more transverse velocity components indicating a direction and a speed of the structure flowing through the tubular object, compute a wall-to-wall segmentation of the tubular object from the image with a combination of the vector flow imaging data and the image, and display the image with the segmentation and the vector flow imaging data superimposed thereover, with the vector flow imaging data extending from wall-to-wall within the tubular object.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following describes an approach that combines VFI data and B-mode imaging to create a wall-to-wall segmentation of walls of a blood vessel represented in a B-mode image or volume. The segmentation can be utilized at least for adaptively adjusting/optimizing a PRF and/or echo cancelling during imaging based on the flow rate determined with the VFI data and the wall-to-wall segmentation and/or determine flow measurements such as peak systolic velocity (PSV), a largest vessel diameter (Dmax), volume flow, etc. based on the VFI data and the wall-to-wall segmentation. For sake of brevity and clarity, the terms "image" and "region" also encompasses the term "volume" herein.

Figure 2:
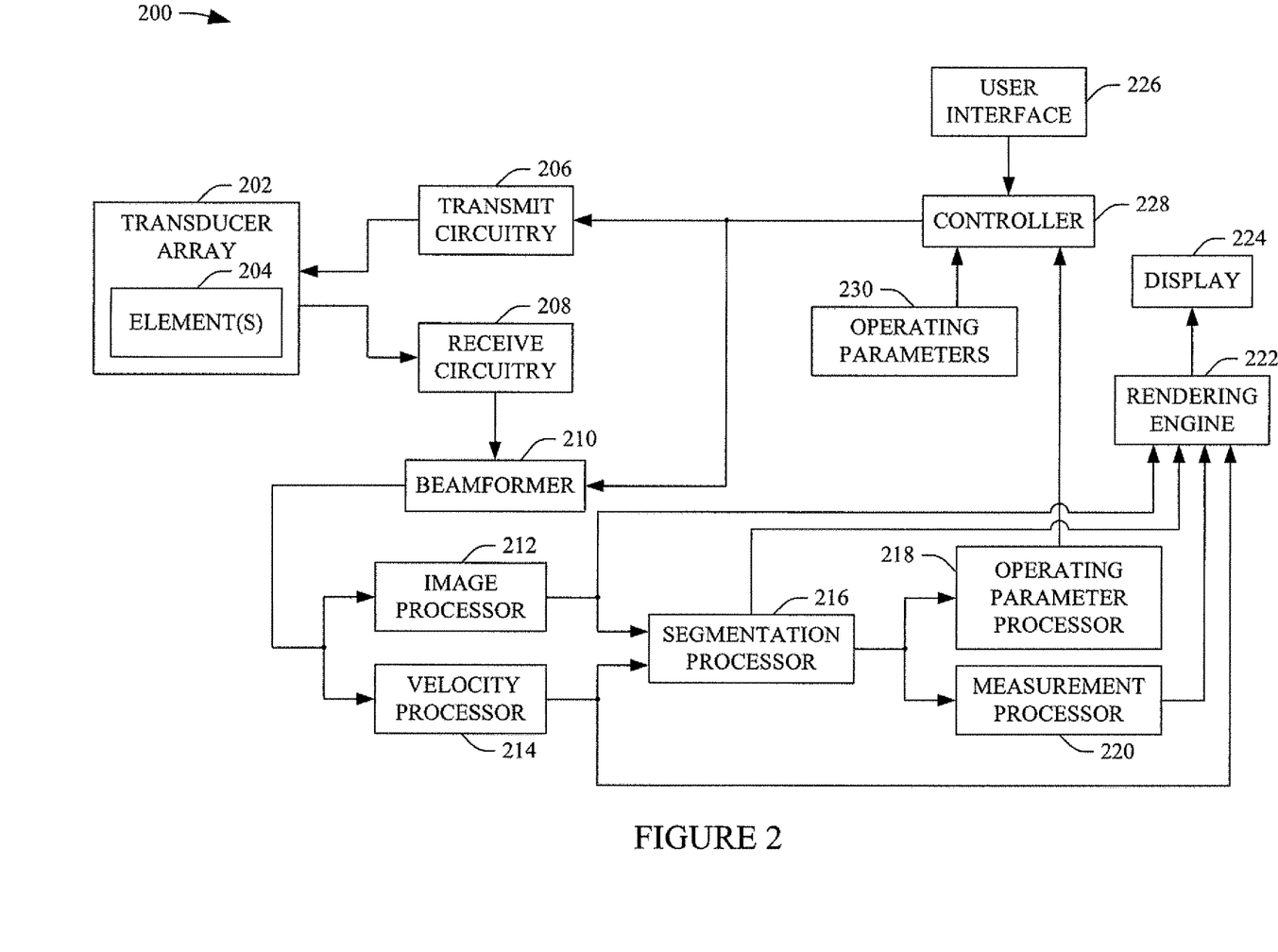
FIG. 2 schematically illustrates an example ultrasound imaging system in accordance with an embodiment described herein.

FIG. 2 schematically illustrates an example ultrasound imaging system 200. A transducer array 202 includes one or more transducer elements 204, which are configured to transmit ultrasound signals. The one or more transducer elements 204 are also configured to receive echo signals and generate electrical signals indicative thereof. The echo signals are produced in response to an interaction between the ultrasound signals and the structure (e.g., flowing blood cells, organ cells, etc.).

The transducer array 202 can be a one or two-dimensional (1-D or 2-D) array. Examples of 1-D arrays include arrays with 8, 16, 32, 64, 96, 128, 512, and/or other number of elements. Examples of 2-D arrays include square, rectangular, circular, row-column, irregular, and/or other arrays. The transducer array 202 can be linear, curved, phased, and/or other array. The transducer array 202 can be fully populated or sparse and/or a combination thereof.

Transmit circuitry 206 generates a set of pulses that are conveyed to the transducer array 202. The set of pulses excites a set of the transducer elements 204, which causes the elements 204 to emit ultrasound signals, optionally with an adaptively determined PRF, which is estimated from a wall-to-wall segmentation of a vessel. Receive circuitry 208 receives the electrical signals. The receive circuitry 208 may amplify, filter, convert analog signals to digital signals, etc. The transducer array 202 may have separate transmit and receive elements, and/or a switch may switch between the transmit and receive circuitry 206 and 208.

A beamformer 210 beamforms the signals by applying time delays to signals, weighting signals, summing delayed and weighted signals, and/or otherwise beamforming received signals, creating a beam of RF data. For VFI, the beamformer 210 produces ultrasound data to estimate an axial velocity component, which extends along a direction of a propagating beam, and at least one transverse velocity component, which extends transverse to the axial velocity component. This may include applying echo cancellation to the beamformed data, where the echo cancellation is optionally optimized based on a wall-to-wall segmentation of a vessel.

An image processor 212 processes the beamformed data and generates an image/volume. For B-mode imaging, this may include, e.g., envelope detection, log-compression, and/or other processing. The image processor 212 may also process scan-lines to lower speckle and/or improve specular reflector delineation, and/or perform other processing such as finite impulse response "FIR" and/or infinite impulse response "IIR" filtering, etc.

A velocity processor 214 processes the pre-processed data and generates VFI data. This includes generating the axial and the one or more transverse velocity components. These velocity components indicate a direction and a speed of flowing structure. Example of determining such components are described in U.S. Pat. No. 6,859,659 B1, filed on Nov. 9, 2001, and entitled "Estimation of Vector Velocity," and application Ser. No. 14/350,500, publication number US 2014/0257103 A1, filed on Apr. 8, 2014, and entitled "Three Dimensional (3D) Transverse Oscillation Vector Velocity Ultrasound Imaging," both of which are incorporated herein by reference in their entireties. Other approaches are also contemplated herein.

A segmentation processor 216 receives both the VFI data and B-mode image/volume. The segmentation processor 216 creates an accurate wall-to-wall segmentation of walls of a blood vessel represented in the B-mode image/volume. As described in greater detail below, this includes generating a marker image/volume from 2-D/3-D VFI information, using the marker image/volume with a marker-controlled region/volume growing algorithm to delineate the vessel boundaries in the B-mode image/volume, rejecting non-vessel structure, and implementing an inter-frame co-registration of segmentations to make sure that vessels segmented in each frame are in correspondence with the same vessels segmented in neighboring frames in the sequence.

Figure 3:
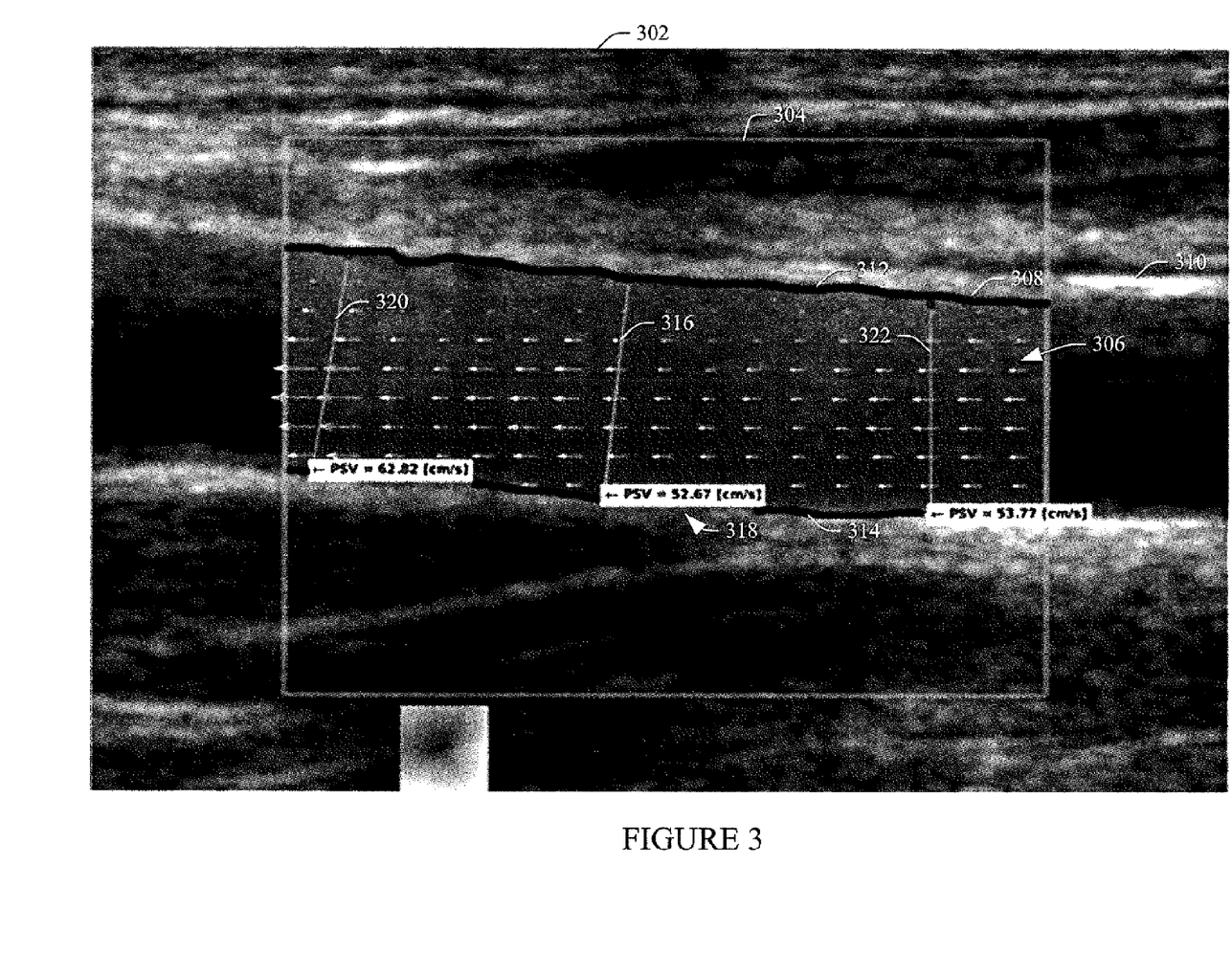
FIG. 3 illustrates an example B-mode image with segmented vessel walls, wall-to-wall, (segmented based on a combination VFI data and the B-mode image) and VFI data superimposed thereover.

Briefly turning to FIG. 3, a B-mode image 302 with a user identified region of interest 304 within which VFI data 306 is superimposed over a sub-portion 308 of a vessel 310, within the sub-portion 308 between vessel walls 312 and 314, is illustrated. Using the segmentation approach described herein, the vessel walls 312 and 314 are accurately segmented, wall-to-wall, based on the combination of the VFI data and B-mode image. In the prior art approach in FIG. 1, without the wall-to-wall delineation described herein, the user has to visually estimate where the vessel walls are, and the superimposed VFI data does not track well to the actual vessel walls 106 and 108 and thus is not available for regions close to the vessel walls for measurement purposes such that velocities are not displayed for those regions.

Returning to FIG. 2, an operating parameter processor 218 receives the segmented vessel walls as an input. In one instance, the operating parameter processor 218 estimates a PRF based on the segmented vessel walls. Operating parameters 230 include the operating PRF which can then be adaptively adjusted to the estimated PRF for further imaging. In general, the operating PRF is adapted based on the vessel delineation without need for manual adjustment by the user, although the user can manually adjust the PRF if desired. The auto adjustment includes a PRF optimized for full visualization of the velocities in the cardiac cycle. For example, the estimated PRF ensures that during systole, when higher velocities are present, a higher PRF is utilized, and during diastole, a lower PRF is utilized. By using the estimated PRF, the generated VFI mask (discussed below) will have the closest boundaries relative to the automated segmentation. In another instance, echo cancelling can be automatically tuned so that it yields the biggest correlation with the segmentation. The optimal echo cancelling occurs when the VFI mask is the closest match to the mask generated from the segmentation procedure.

A measurement processor 220 also receives the segmented vessel walls as an input. The measurement processor 220 processes the segmented vessel walls to extract certain features, and then determines one or more measurements from these features. For an automated PSV measurement, the measurement processor 220 determines PSV along a line along a cross section of the vessel based on the delineated vessel of the segmentation. In FIG. 3, with the accurate identification of the vessel walls 310 and 314, the measurement processor 220 can identify a path 316 from wall to wall, perpendicular to each wall, and compute a PSV 318 along the path 316. In FIG. 1, without the vessel delineation from the segmentation, the user has to manually place the path or flow measurement line 120 without the segmentation, which may lead to a less accurate PSV measurement.

Returning to FIG. 2, for an automated largest vessel diameter measurement for abdominal aortic aneurysms assessment, the measurement processor 220 computes a maximum diameter of the vessel during a cardiac cycle using the accurate vessel wall delineation of the segmentation. For example, in FIG. 3, the measurement processor 220 can determine a diameter for the wall-to-wall path 316 by a length of the path 316. In one instance, this enables clinicians to use VFI to automatically diagnose the aneurysms while scanning the vessel, without performing manual measurement on the scans. For abdominal aortic aneurysms assessment, a focal dilatation in an artery, with at least a 50% increase of its normal diameter, is defined as an aneurysm. An enlargement larger than three centimeters (3 cm) of the abdominal aorta, even if asymptomatic, has been considered in the literature to be an abdominal aortic aneurysm.

Returning to FIG. 2, the measurement processor 220 is also configured to estimate volume flow using the vessel wall delineation of the segmentation by automatically selecting vessel cross-sections (316, 320, 322, etc.) between the segmented walls for computing the volume flow in VFI. Volume flow quantifies the flow and characterizes the vessel, and the reliability of this measure depends on the estimated vessel diameter. In FIG. 3, with the accurate identification of the vessel walls 310 and 314, the VFI data extends from wall-to-wall (the entire vessel region), and velocities can be computed for the entire vessel sub-portion 308. As such, the approach described herein enables correct estimation of the volume flow, and computes volume flow without manual intervention of user.

Figure 4:
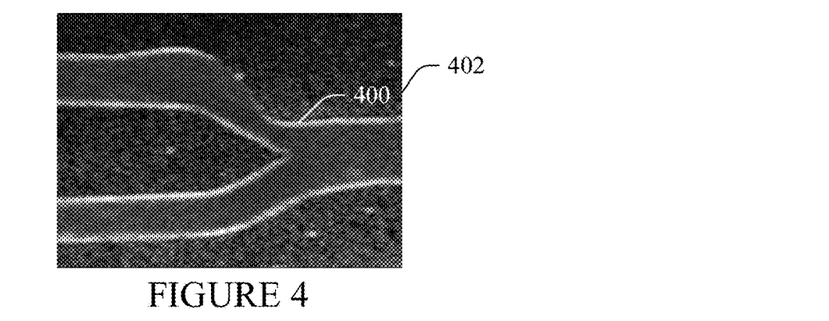
FIG. 4 illustrates another example B-mode image with segmented vessel walls, wall-to-wall, (segmented based on a combination VFI data and the B-mode image) superimposed thereover.
Figure 5:
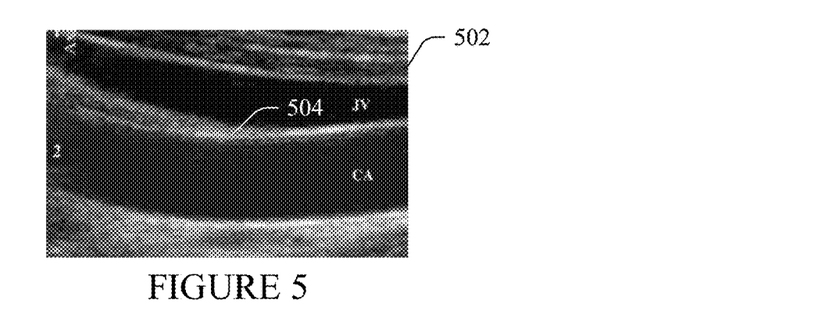
FIG. 5 illustrates another example B-mode with segmented vessel walls, wall-to-wall, (segmented based on a combination VFI data and the B-mode image) superimposed thereover.

Returning to FIG. 2, a rendering engine 222 receives the B-mode image/volume, the VFI data, the segmentation, and, if take, the measurement(s) and displays, via a display 224 and/or other display, one or more of the B-mode image/volume, the VFI data, the segmentation, and/or the measurement(s). For example, the rendering engine 222 can display only the B-mode image/volume, the B-mode image/volume with the VFI data superimposed thereover, the B-mode image/volume with the segmented vessel wall superimposed thereover the B-mode image/volume with the VFI data and segmented vessel wall superimposed thereover, the B-mode image/volume with the VFI data, segmented vessel wall, and measurement superimposed thereover, etc. FIGS. 4 and 5 show examples of B-mode images 402 and 502 with wall-to-wall segmentation of vessels 404 and 504 superimposed thereover.

Returning to FIG. 2, a user interface 226 includes one or more input devices (e.g., a button, a knob, a slider, a touch pad, a mouse, a trackball, a touch screen, etc.) and/or one or more output devices (e.g., a display screen, a light, an audio generator, etc.), which allow for interaction between a user and the ultrasound imaging system 200. A controller 228 controls one or more of the components 202, 204, 206, 208, 210, 212, 214, 216, 218, 220 and 222, e.g., based on one or more modes of operation (e.g., VFI+B-mode, measurement mode, auto PRF, echo cancelation, etc.). In one instance, this includes adjusting the operating PRF based on the PRF estimated by the operating parameter processor 218 and/or a signal from the user interface 226 adjusting the PRF, optimizing echo cancelling based on the segmentation, etc.

One or more of the beamformer 210, the image processor 212, the velocity processor 214, the segmentation processor 216, the operating parameter processor 218, the measurement processor 220 and/or other component(s) can be implemented via one or more processors (e.g., a central processing unit CPU, a microprocessor, a controller, a graphics processing unit GPU, etc.) executing one or more computer readable instructions encoded or embedded on computer readable storage medium (which excludes transitory medium) such as physical memory or other non-transitory medium. Additionally or alternatively, at least one of the instructions can be carried by a carrier wave, a signal, or other transitory medium.

It is to be understood that the ultrasound imaging system 200 can be part of a portable system on a stand with wheels, a system residing on a tabletop, and/or other system in which the transducer array 202 is housed and mechanically supported in a probe or the like and one or more of the other components (e.g., one or more of the components 206, 208, 210, 212, 214, 216, 218, 220, 222, 224, 226, 228 and 230) are housed and mechanically supported in a console, which is separate from the probe. The display 224 may or may not be part of the console. In another instance, the transducer array 202 and one or more of the other components are housed and/or mechanically supported within a single enclosure hand-held ultrasound scanning device.

In a variation, at least one of the operating parameter processor 218 or the measurement processor 220 is omitted.

Figure 6:
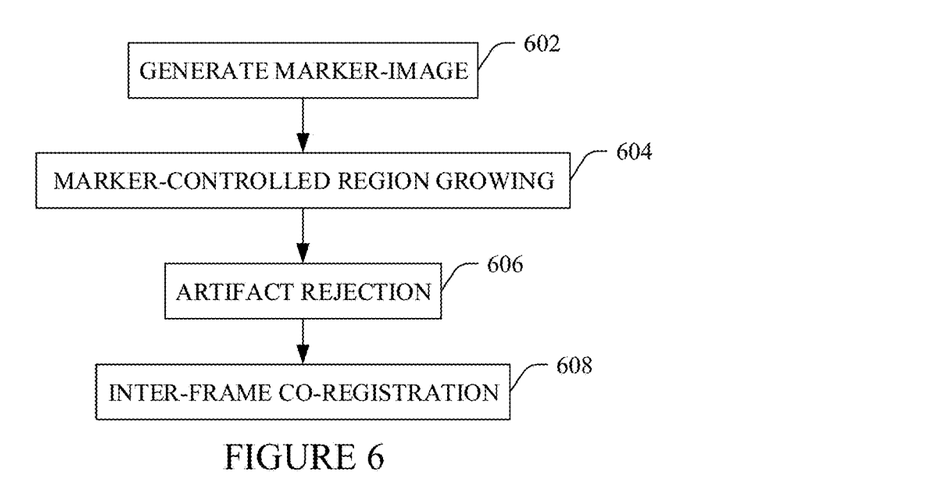
FIG. 6 illustrates an example segmentation algorithm based on a combination VFI data and a B-mode image.

As briefly discussed above, the segmentation processor 216 processes the VFI flow data and the B-mode image/volume and creates a wall-to-wall segmentation for a blood vessel. FIG. 6 illustrates an example segmentation algorithm in connection with 2-D VFI data and a 2-D B-mode image. However, it is to be understood that one skilled in the art would know how to adjust the algorithm without undue experimentation for 3-D VFI data and a 3-D B-mode volume to generate a marker volume and use this maker volume in a volume growing algorithm with respect to the B-mode volume to delineate vessel boundaries in 3-D. Generally, the segmentation of FIG. 6 can be divided into the below described four distinct steps.

1) Step I (602): Generating a Marker-Image.

Figure 7:
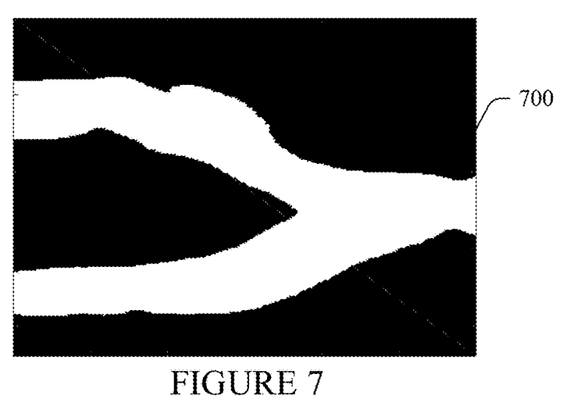
FIGS. 7-10 illustrate examples of the segmentation for a first step of the segmentation algorithm of FIG. 6.

With reference to FIGS. 2 and 6-10, the segmentation processor 216 detects inner markers and outer markers. The segmentation processor 216 detects inner markers using gray scale skeletonization of the VFI data. In one instance, the flow data are absolute velocities of VFI estimates. The skeletonization process extracts a center-line of the flow data that also indicates locations inside the vessel boundary. The skeletonization starts by computing a distance transform 800 (FIG. 8) of an inverted binary mask of VFI data 700 (FIG. 7).

Figure 8:
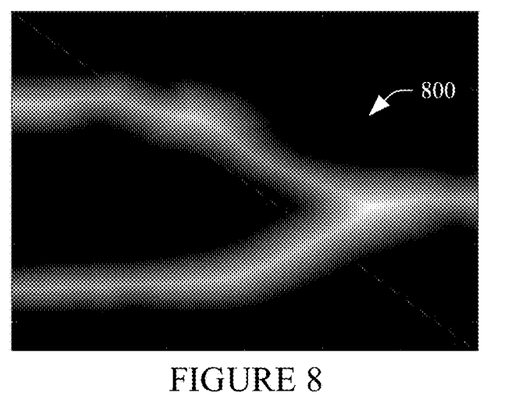
Figure 9:
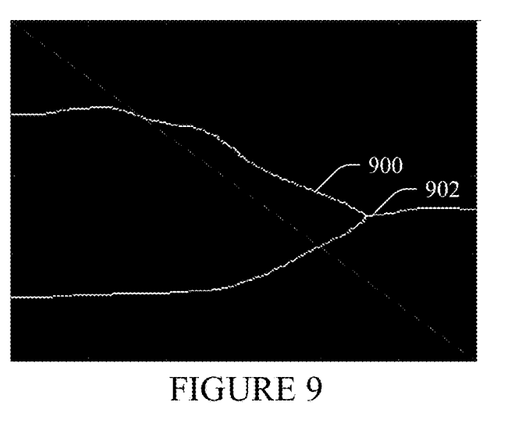

Ridge lines 900 on the distance transform 800 are extracted as a centerline 902 of the flow data (FIG. 9). The centerline 902 is the inner marker.

Figure 10:
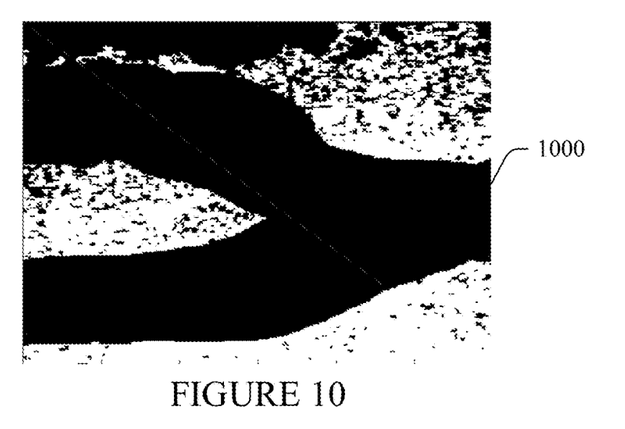
Figure 11:
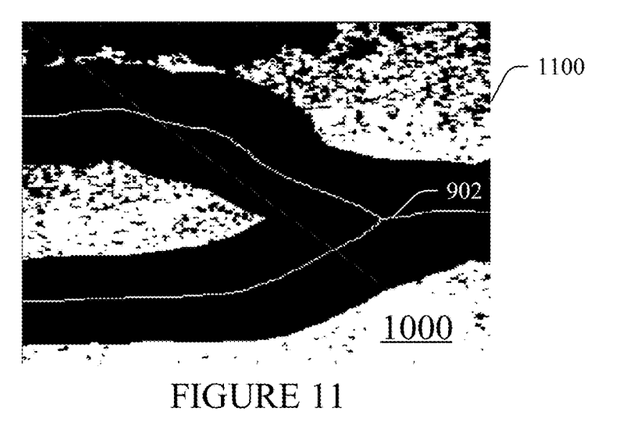
FIGS. 11 and 12 illustrate examples of the segmentation for a second step of the segmentation algorithm of FIG. 6.

The segmentation processor 216 detects outer markers using the B-mode image. Strong specular regions are extracted from the B-mode image and used as an indication of regions outside the vessels. For this purpose, the envelope of the acquired scan is first computed. A cumulative histogram of the intensity values is then generated. The intensity values less than half of the maximum intensities in the envelope are disregarded, and a mask of strong signal regions is generated. The mask is then multiplied to a dilated version of the VFI mask and yields an outer marker mask 1000 (FIG. 10). FIG. 11 shows a marker-image 1100 including the outer marker mask 1000 with the centerline 902.

2) Step II (604): Marker-Controlled Region Growing.

With reference to FIGS. 2, 6, 11, and 12, the segmentation processor 216 employs a marker-controlled watershed image processing approach to delineate or segment boundaries of vessel-like structures bracketed by the marker-image 1100. The B-mode image is median filtered, and a watershed segmentation of this filtered image with respect to the marker-image yields a segmentation 1200 of the vessel-like structures.

Figure 12:
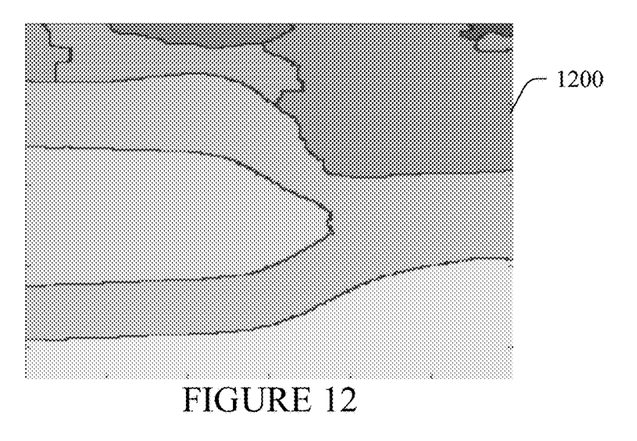

(FIG. 12)

3) Step III (606): Artifact Rejection.

Figure 13:
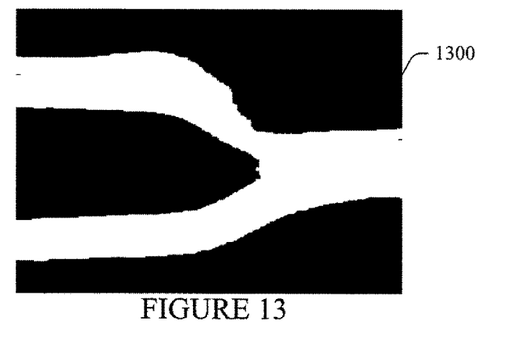
FIG. 13 illustrates an example of the segmentation for a third step of the segmentation algorithm of FIG. 6.

With reference to FIGS. 2, 6 and 13, the segmentation processor 216 reduces over-segmented regions (resulting from the region growing), which do not belong to the vessel regions. For this, in one instance, the segmentation processor 216 employs artifact rejection based on size, shape and/or vascularity (e.g., using a vesselness filter such as a Frangi filter or the like to ensure that only vessels are retained). Basically elongated objects containing flow data are kept in segmentation results and the rest are excluded. Even though, the retained structures in this step are vessel-like objects, the boundaries of vessels might have some discrepancies to the actual vessel boundaries. FIG. 13 shows an example image 1300 in which in which artifacts are rejected and vessel-like structures are retained.

4) Step IV (608): Inter-Frame Co-Registration of Segmentations.

Returning to FIG. 2, the segmentation processor 216 corrects the segmentation so that it follows the vessel boundaries using an inter-frame co-registration of the segmentations. To refine parts of the segmentation that does not follow the actual vessel boundaries, a few neighboring frames in time are considered. Segmentations of those frames are co-registered and regions matching in at least a sub-portion (e.g., 50% to 100%, such as 80%, 85%, etc.) of frames are considered to be the actual vessel.

Figure 14:
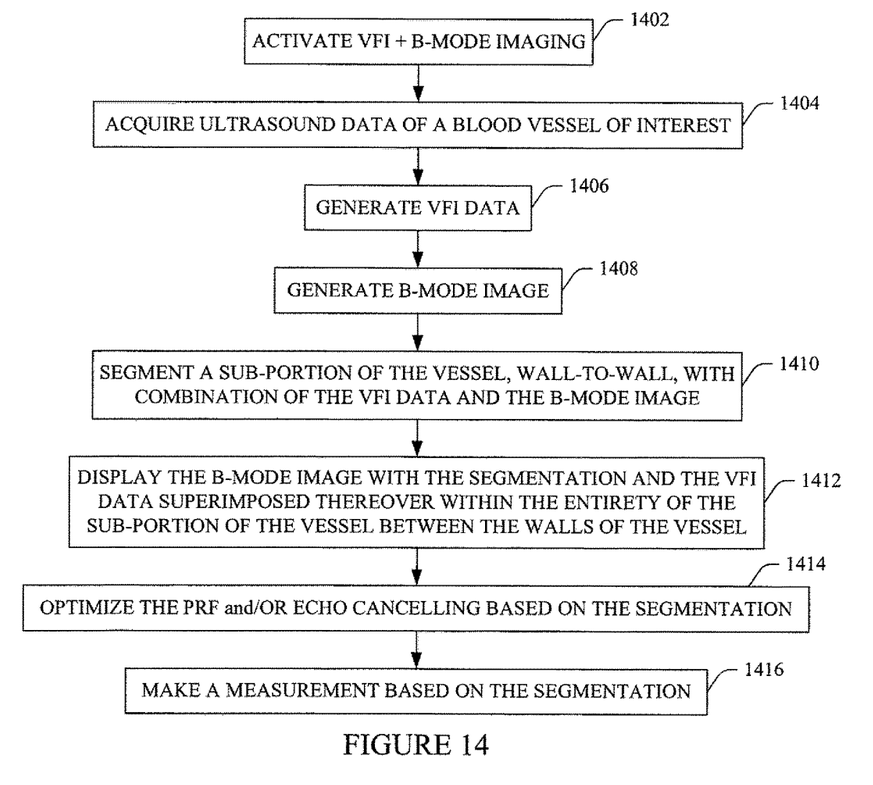
FIG. 14 illustrates an example segmentation method in accordance with an embodiment described herein.

FIG. 14 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 1402, VFI+B-mode imaging is activated for the system 200.

At 1404, the transducer 202 is employed to scan a subject and acquire ultrasound data of a blood vessel(s) of interest.

At 1406, VFI data is generated with the acquired ultrasound data.

At 1408, a B-mode image is generated with the acquired ultrasound data.

At 1410, a sub-portion of a blood vessel(s) in a region of interest is segmented wall-to-wall using a combination of the VFI data and the B-mode image, as described herein and/or otherwise.

At 1412, the B-mode image is displayed with the segmentation and the VFI data superimposed thereover within the entirety of the sub-portion of the blood vessel between the walls.

At 1414, at least one of the PRF or echo cancellation is optimized based on the wall-to-wall vessel segmentation, as described herein and/or otherwise.

At 1416, at least one measurement it made based on the wall-to-wall vessel segmentation, as described herein and/or otherwise.

In a variation, at least one of act 1414 or 1416 is omitted.

The methods described herein may be implemented via one or more processors executing one or more computer readable instructions encoded or embodied on computer readable storage medium such as physical memory, which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound system, comprising:
an image processor configured to process beamformed ultrasound data representing structure flowing through a tubular object and generate an image indicative of the tubular object based thereon;
a velocity processor configured to process the beamformed ultrasound data and generate vector flow imaging data indicative of the structure flowing through the tubular object based thereon, wherein the vector flow imaging data includes at least an axial velocity component signal and one or more transverse velocity components indicating a direction and a speed of the structure flowing through the tubular object;
a segmentation processor configured to segment the tubular object from the image based on a combination of both the vector flow imaging data and the image, wherein a resulting segmentation extends from wall-to-wall of the tubular object, wherein the segmentation processor segments the tubular object by:
generating a single marker image from the vector flow imaging data and the image by:
detecting inner markers through a gray scale skeletonization of only the vector flow imaging data to extract a center line of the vector flow imaging data by generating a distance map of an inverse of a velocity flow imaging binary mask and extracting ridge lines on the distance map as the center line, which indicates locations inside a boundary of the tubular object;
detecting outer markers by extracting strong specular regions, which are outside of the tubular structure, from the image to generate a binary mask containing the strong specular regions and multiplying the binary mask by a dilated version of a velocity flow information mask to generate an outer marker mask that highlights the strong specular regions and does not cover an area with flow; and combining the inner and outer markers into the single marker image; and a display configured to display the image with the segmentation and the vector flow imaging data superimposed thereover, with the vector flow imaging data extending from wall-to-wall within the tubular object.

2. The system of claim 1, wherein the segmentation processor further segments the tubular object by:

using the marker image with a marker-controlled watershed image region growing algorithm to delineate tubular object boundaries in the image;

rejecting non-tubular object structure based on at least one of a size, a shape, an amount of flow, or a vascularity to ensure only tubular structure is retained; and employing an inter-frame co-registration of segmentations across frames to ensure a tubular object segmented in each frame are in correspondence with a same tubular object segmented in neighboring frames in a sequence, wherein tubular objects matching in all frames are considered to be the actual tubular structure.

3. The system of claim 2, wherein the segmentation processor determines an inner marker from the vector flow imaging data, an outer marker from only the image and the vector flow imaging data, and combines the inner and outer markers to produce the marker image.

4. The system of claim 3, wherein the segmentation processor determines the inner marker by employing a gray scale skeletonization of the vector flow imaging data, wherein the skeletonization includes extracting a center line of the vector flow imaging data, which indicates locations inside the tubular object boundary.

5. The system of claim 4, wherein the segmentation processor extracts the center line by generating a distance map of an inverse of a velocity flow imaging binary mask, and extracting ridge lines on the distance map as the center line.

6. The system of claim 3, wherein the segmentation processor determines the outer marker by extracting strong specular regions from the image, which are considered outside of the tubular structure.

7. The system of claim 2, wherein the segmentation processor employs a marker-controlled watershed image processing approach, using the marker image, to segment boundaries of tubular-like structures located by the marker image.

8. The system of claim 7, wherein the segmentation processor generates a binary mask containing strong specular regions, and multiplies the binary mask by a dilated version of a velocity flow information mask, which generates an outer marker mask that highlights the strong specular regions and ensures the mask does not cover an area with flow.

9. The system of claim 2, wherein the segmentation processor rejects non-tubular object structure based on at least one of a size, a shape, an amount of flow, and/or a vascularity to ensure only tubular structure is retained.

10. The system of claim 1, further comprising:

an operating parameter processor configured to adaptively adjust a pulse repetition frequency during imaging based on the wall-to-wall segmentation.

11. The system of claim 1, further comprising:

an operating parameter processor configured to tune echo cancelling during imaging based on the wall-to-wall segmentation.

12. The system of claim 1, further comprising:

a measurement processor configured to estimate a peak systolic velocity based on the wall-to-wall segmentation.

13. The system of claim 1, further comprising:

a measurement processor configured to estimate a largest vessel diameter based on the wall-to-wall segmentation.

14. The system of claim 1, further comprising:

a measurement processor configured to estimate a volume flow based on the wall-to-wall segmentation.

15. A method, comprising:

generating an image indicative of a tubular object from beamformed ultrasound data representing structure flowing through the tubular object;

generating vector flow imaging data indicative of the structure flowing through the tubular object from beamformed ultrasound, wherein the vector flow imaging data includes at least an axial velocity component signal and one or more transverse velocity components indicating a direction and a speed of the structure flowing through the tubular object;

generating a wall-to-wall segmentation of the tubular object from the image with a combination of the vector flow imaging data and the image by:

detecting inner markers through a gray scale skeletonization of only the vector flow imaging data to extract a center line of the vector flow imaging data by generating a distance map of an inverse of a velocity flow imaging binary mask and extracting ridge lines on the distance map as the center line, which indicates locations inside a boundary of the tubular object;

detecting outer markers by extracting strong specular regions, which are outside of the tubular structure, from the image to generate a binary mask containing the strong specular regions and multiplying the binary mask by a dilated version of a velocity flow information mask to generate an outer marker mask that highlights the strong specular regions and does not cover an area with flow; and combining the inner and outer markers into the single marker image; and visually presenting the image with the segmentation and the vector flow imaging data superimposed thereover, with the vector flow imaging data extending from wall-to-wall within the tubular object.

16. The method of claim 15, wherein generating a wall-to-wall segmentation includes:

using the marker image with a marker-controlled watershed image region growing algorithm to delineate tubular object boundaries in the image;

rejecting non-tubular object structure; and employing an inter-frame co-registration of segmentations across frames to make sure that a tubular object segmented in each frame are in correspondence with a same tubular object segmented in neighboring frames in a sequence.

17. The method of claim 16, wherein non-tubular object structure is rejected based on at least one of a size, a shape, an amount of flow, and/or a vascularity to ensure only tubular structure is retained.

18. The method of claim 17, wherein employing the inter-frame co-registration includes identifying only regions of neighboring frames in time matching in at least 80% of the frames as the actual tubular structure.

19. The method of claim 16, further comprising:
at least one of adaptively adjusting a pulse repetition frequency during imaging based on the segmentation or tuning echo cancelling during imaging based on the segmentation.

20. The method of claim 16, further comprising:
at least one of estimating a peak systolic velocity based on the segmentation, estimating a largest vessel diameter based on the segmentation, or estimating a volume flow based on the segmentation.

21. A computer readable storage medium encoded with computer readable instructions, which, when executed by a processor, causes the processor to:
construct an image indicative of a tubular object from beamformed ultrasound data representing structure flowing through the tubular object;
estimate vector flow imaging data indicative of the structure flowing through the tubular object from beamformed ultrasound, wherein the vector flow imaging data includes at least an axial velocity component signal and one or more transverse velocity components indicating a direction and a speed of the structure flowing through the tubular object;
compute a wall-to-wall segmentation of the tubular object from the image with a combination of the vector flow imaging data and the image by:
detecting inner markers through a gray scale skeletonization of only the vector flow imaging data to extract a center line of the vector flow imaging data by generating a distance map of an inverse of a velocity flow imaging binary mask and extracting ridge lines on the distance map as the center line, which indicates locations inside a boundary of the tubular object;
detecting outer markers by extracting strong specular regions, which are outside of the tubular structure, from the image to generate a binary mask containing the strong specular regions and multiplying the binary mask by a dilated version of a velocity flow information mask to generate an outer marker mask that highlights the strong specular regions and does not cover an area with flow; and
combining the inner and outer markers into the single marker image; and
display the image with the segmentation and the vector flow imaging data superimposed thereover, with the vector flow imaging data extending from wall-to-wall within the tubular object.

* * * * *